United States Patent
Adams et al.

(10) Patent No.: US 7,329,470 B2
(45) Date of Patent: Feb. 12, 2008

(54) APPARATUS AND METHOD FOR IN SITU PRODUCTION OF FUEL FOR A FUEL CELL

(75) Inventors: Paul Adams, Monroe, CT (US);
Andrew J. Curello, Hamden, CT (US);
Floyd Fairbanks, Naugatuck, CT (US)

(73) Assignee: Societe BIC, Clichy Cedex ( * ) Notice: Subject to any disclaimer, the term of this patent is extended or adjusted under 35 U.S.C. 154(b) by 293 days.

(21) Appl. No.: 10/854,540

(22) Filed: May 26, 2004

(65) Prior Publication Data

US 2005/0266281 A1   Dec. 1, 2005

(51) Int. Cl.
*H01M 8/06* (2006.01)
*B65D 6/00* (2006.01)

(52) U.S. Cl. ............... 429/19; 429/17; 429/34

(58) Field of Classification Search ............ None
See application file for complete search history.

(56) References Cited

U.S. PATENT DOCUMENTS

| | | | |
|---|---|---|---|
| 3,609,191 A | 9/1971 | Wade | |
| 3,928,293 A | 12/1975 | Crosby | |
| 4,355,140 A | 10/1982 | Manziek | |
| 4,410,665 A | 10/1983 | Manziek | |
| 5,866,182 A | 2/1999 | Exner et al. | |
| 5,945,231 A | 8/1999 | Narayanan et al. | |
| 5,992,008 A | 11/1999 | Kindler | |
| 6,433,129 B1 | 8/2002 | Amendola et al. | |
| 6,506,513 B1 | 1/2003 | Yonetsu et al. | |
| 6,517,798 B1 | 2/2003 | Schirmann | |
| 6,544,400 B2 | 4/2003 | Hockaday | |
| 6,563,207 B2 | 5/2003 | Shinma | |
| 6,586,563 B1 | 7/2003 | Ortega et al. | |
| 6,645,651 B2 * | 11/2003 | Hockaday et al. | 429/19 |
| 6,924,054 B2 * | 8/2005 | Prasad et al. | 429/34 |
| 6,989,120 B2 | 1/2006 | Mathur | |
| 2001/0045364 A1 * | 11/2001 | Hockaday et al. | 205/338 |
| 2002/0012737 A1 | 1/2002 | Kirby et al. | |
| 2003/0077493 A1 | 4/2003 | Colborn et al. | |
| 2003/0082427 A1 | 5/2003 | Prasad et al. | |
| 2003/0096150 A1 | 5/2003 | Rice et al. | |
| 2005/0081433 A1 | 4/2005 | Ren | |

OTHER PUBLICATIONS

"Analysis of Hydrogen Production Using Ammonia and Ammonia-Borane Complex for Fuel Cell Applications," Hydrogen, Fuel Cells, and Infrastructure Technologies, FY 2002 Progress Report, Ali T-Raissi, at http://www.eere.energy.gov/hydrogenandfuelcells/pdfs/33098_sec5.pdf, no month.

(Continued)

*Primary Examiner*—John S. Maples
(74) *Attorney, Agent, or Firm*—The H.T. Than Law Group

(57) ABSTRACT

Fuel cell fuel supplies having single and multiple compartments for storing and containing fuel cell fuel precursor reagents. These fuel supplies allow storage and packaging of precursors for in situ production and use of fuel cell fuel. A method for making fuel cell fuel and a fuel cell system is also disclosed.

30 Claims, 2 Drawing Sheets

OTHER PUBLICATIONS

"Opinion of the Scientific Committee on Food on the use of dimethyl dicarbonate (DMDC) in wines (opinion expressed on Jul. 11, 2001)," European Commission, Health & Consumer Protection Directorate-General, Scientific Committee on Food, SCF/CS/ADD/CONS/43 Final, Jul. 12, 2001, Brussel, Belgium.

Franson, Paul; "The Threat of Brett," Vineyard & Winery, at http://www.vwm-online.com/Magazine/Archive/2001/vol27_No5/Brett.htm, no date.

Portable Area Monitor for Velcorin®, "Autostep™ Plus for Velcorin® Brand Cold Beverage Sterilant Model No. 2740-0035", no date.

Walton, Tina; "A Portable Hydrogen Generator," The Alchemist, Sep. 30, 2003, at http://www.chemweb.com/alchem/articles/1063811899357.html.

* cited by examiner

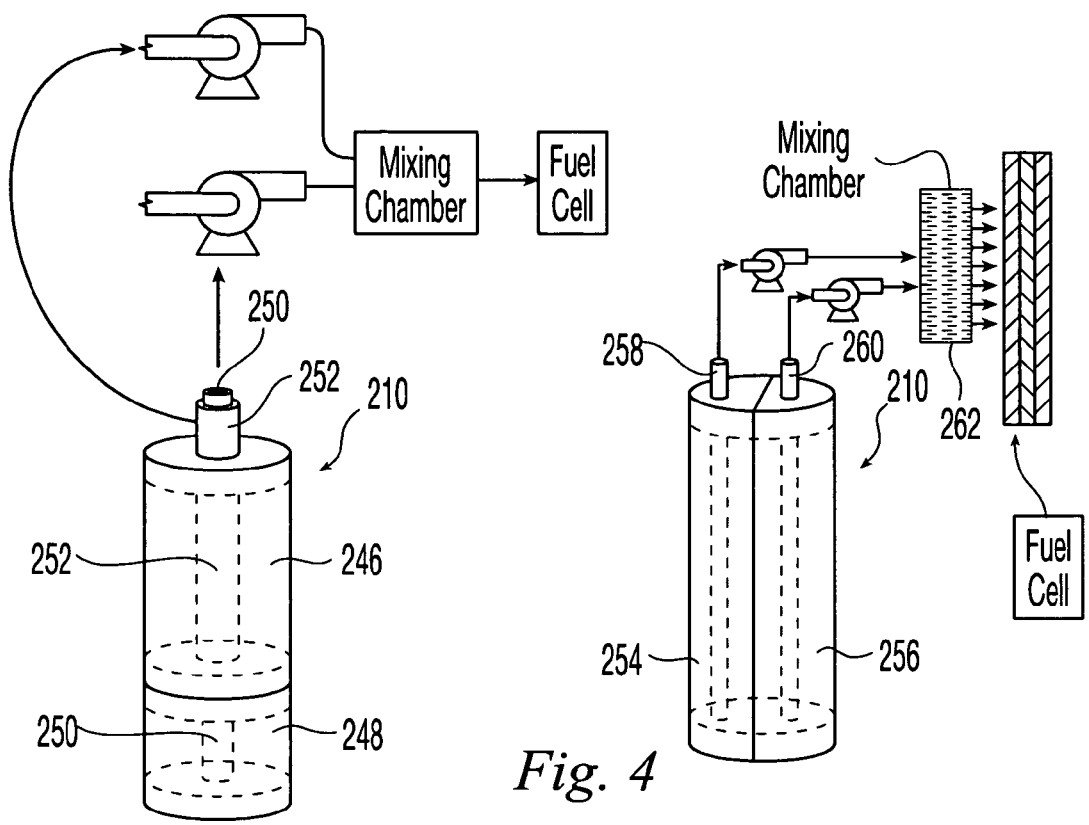
Fig. 3
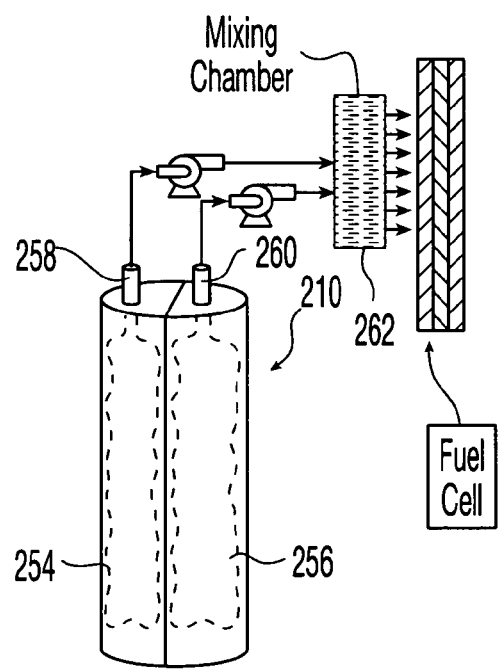
Fig. 4
Fig. 4a

APPARATUS AND METHOD FOR IN SITU PRODUCTION OF FUEL FOR A FUEL CELL

FIELD OF THE INVENTION

This invention generally relates to an apparatus and method for producing fuel. This invention more particularly relates to a fuel system and method for the production of fuel for use in a fuel cell.

BACKGROUND OF THE INVENTION

Fuel cells are devices that directly convert chemical energy of reactants, i.e., fuel and oxidant, into direct current (DC) electricity. For an increasing number of applications, fuel cells are more efficient than conventional power generation, such as combustion of fossil fuel and more efficient than portable power storage, such as lithium-ion batteries.

In general, fuel cell technologies include a variety of different fuel cells, such as alkali fuel cells, polymer electrolyte fuel cells, phosphoric acid fuel cells, molten carbonate fuel cells, solid oxide fuel cells and enzyme fuel cells. Some fuel cells utilize compressed hydrogen ($H_2$) as fuel. Compressed hydrogen is generally kept under high pressure, and is therefore difficult to handle. Furthermore, large storage tanks are typically required and cannot be made sufficiently small for consumer electronic devices. Proton exchange membrane (PEM) fuel cells use methanol ($CH_3OH$), sodium borohydride ($NaBH_4$), hydrocarbons (such as butane) or other fuels reformed into hydrogen fuel. Conventional reformat fuel cells require reformers and other vaporization and auxiliary systems to convert fuel to hydrogen to react with oxidant in the fuel cell. Recent advances make reformer or reformat fuel cells promising for consumer electronic devices. Other PEM fuel cells use methanol ($CH_3OH$) fuel directly ("direct methanol fuel cells" or DMFC). DMFC, where methanol is reacted directly with oxidant in the fuel cell, is the simplest and potentially smallest fuel cell, and also has promising power application for consumer electronic devices. Solid oxide fuel cells (SOFC) convert hydrocarbon fuels, such as butane, at high heat to produce electricity. SOFC requires relatively high temperature over 800° C. for the fuel cell reaction to occur.

The chemical reactions that produce electricity are different for each type of fuel cell. For DMFC, the chemical-electrical reaction at each electrode and the overall reaction for a direct methanol fuel cell are described as follows:

Half-reaction at the anode:

$$CH_3OH + H_2O \rightarrow CO_2 + 6H^+ + 6e^-$$

Half-reaction at the cathode:

$$1.5O_2 + 6H^+ + 6e^- \rightarrow 3H_2O$$

The overall fuel cell reaction:

$$CH_3OH + 1.5O_2 \rightarrow CO_2 + 2H_2O$$

Due to the migration of the hydrogen ions ($H^+$) through the PEM from the anode to the cathode and due to the inability of the free electrons ($e^-$) to pass through the PEM, the electrons must flow through an external circuit, thereby producing an electrical current through the external circuit. The external circuit may be used to power many useful consumer electronic devices, such as mobile or cell phones, calculators, personal digital assistants, laptop computers, and power tools, among others.

DMFC is discussed in U.S. Pat. Nos. 5,992,008 and 5,945,231, which are incorporated by reference in their entireties. Generally, the PEM is made from a polymer, such as Nafion® available from DuPont, which is a perfluorinated material having a thickness in the range of about 0.05 mm to about 0.50 mm, or other suitable membranes. The anode is typically made from a Teflonized carbon paper support with a thin layer of catalyst, such as platinum-ruthenium, deposited thereon. The cathode is typically a gas diffusion electrode in which platinum particles are bonded to one side of the membrane.

Another fuel cell reaction for a sodium borohydride reformer fuel cell is as follows:

$$NaBH_4(aqueous) + 2H_2O \rightarrow (heat\ or\ catalyst) \rightarrow 4(H_2) + (NaBO_2)(aqueous)$$

Half-reaction at the anode:

$$H_2 \rightarrow 2H^+ + 2e^-$$

Half-reaction at the cathode:

$$2(2H^+ + 2e^-) + O_2 \rightarrow 2H_2O$$

Suitable catalysts for this reaction include platinum and ruthenium, and other metals. The hydrogen fuel produced from reforming sodium borohydride is reacted in the fuel cell with an oxidant, such as $O_2$, to create electricity (or a flow of electrons) and water byproduct. Sodium borate ($NaBO_2$) byproduct is also produced by the reforming process. A sodium borohydride fuel cell is discussed in United States published patent application no. 2003/0082427, which is incorporated herein by reference.

One of the more important features for fuel cell application is fuel storage. The fuel supply should also be easily inserted into the fuel cell or the electronic device that the fuel cell powers. Additionally, the fuel supply should also be easily replaceable or refillable.

United States published patent publication no. 2003/0082427 discloses a fuel cartridge where sodium borohydride fuel is reformed within the cartridge to form hydrogen and byproduct. However, the prior art does not disclose a fuel supply that allows in situ production of fuel or that contains reagents amenable to non-corrosive, low cost storage, or fuel supplies with the advantages and features described below.

SUMMARY OF THE INVENTION

Hence, the present invention is directed to a fuel supply that allows in situ production of fuel for a fuel cell.

The present invention is also directed to a fuel supply that contains precursor reagents that can react to form fuel for a fuel cell.

One aspect of the present invention is directed to a fuel supply allowing in situ production of fuel for a fuel cell. This fuel supply has a first compartment that contains a first precursor reagent. The system also includes a second compartment that contains a second precursor reagent such that the contents of the first container and the second container are mixable to create a fuel that powers the fuel cell.

Another aspect of the invention is directed to a method for producing fuel for a fuel cell that comprises the step of providing a fuel cell fuel supply having a first compartment that contains a first precursor reagent. It also comprises the step of causing the first precursor reagent to react with a second precursor reagent to form the fuel. The reaction can occur within the fuel supply or outside of the fuel supply.

BRIEF DESCRIPTION OF THE DRAWINGS

In the accompanying drawings, which form a part of the specification and are to be read in conjunction therewith and in which like reference numerals are used to indicate like parts in the various views:

FIG. 3 is a schematic view of another fuel cartridge having top and bottom compartments in accordance with another embodiment of the present invention wherein fuel precursor reagents mix outside of the cartridge; and FIGS. 4 and 4A are schematic views of other fuel cartridges having side-by-side compartments in accordance with another embodiment of the present invention wherein fuel precursor reagents mix outside of the cartridge.

DETAILED DESCRIPTION OF THE PREFERRED EMBODIMENTS

Figure 1:
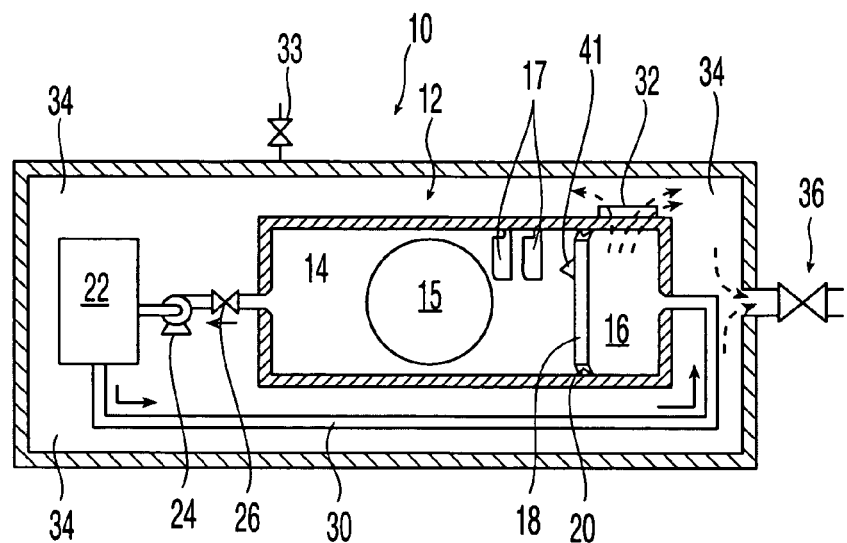
FIG. 1 is a cross-sectional view of a fuel cartridge in accordance with one embodiment of the present invention having multiple precursor reagent compartments.

As illustrated in the accompanying drawings and discussed in detail below, one aspect of the present invention is directed to a fuel supply that contains one or more precursors to a fuel for a fuel cell. Such fuel includes, for example, methanol/water mixtures of varying concentrations, borohydrides, borane, and hydrazine. Suitable precursor(s) include, for example, water, dimethyl dicarbonate, borane-containing polymers, sodium carbonate, azine, hydrogen peroxide, ammonia, and methylethyl ketone.

Another aspect of the present invention is directed to a method for making fuel for a fuel cell. This method includes the step of combining one or more precursor reagents from a fuel supply with one (or more) other precursor reagent(s) from inside or outside of the same fuel supply. The reaction between the precursor reagent(s) can occur inside or outside of the fuel supply.

Another aspect of the present invention is similarly directed to a fuel system containing one or more precursors to a fuel for a fuel cell.

The present invention further covers precursors in addition to the above-mentioned precursors for any type of fuel cell fuels, as described below. Such additional fuels include, but are not limited to, ethanol or other alcohols, chemicals that can be reformatted into hydrogen, or other chemicals that may improve the performance or efficiency of fuel cells. Fuels suitable for use in this invention therefore also include a mixture of methanol, hydrogen peroxide and sulfuric acid, which flows past a catalyst formed on silicon chips to create a fuel cell reaction. Suitable fuels further include hydrocarbon fuels as well, which include, but are not limited to, butane, kerosene, alcohol and natural gas, disclosed in United States published patent application no. 2003/0096150, entitled "Liquid Hereto-Interface Fuel Cell Device," published on May 22, 2003, which is incorporated herein by reference in its entirety. Suitable fuels also include liquid oxidants that react with fuels. The present invention is, therefore, not limited to any type of fuels, electrolytic solutions, oxidant solutions, liquids, or solids contained in the fuel supply or otherwise used by the fuel cell system. The term "fuel" as used herein includes all fuels that can be reacted in fuel cells, and includes, but is not limited to, all of the above suitable fuels, electrolytic solutions, oxidant solutions, liquids, solids, and/or chemicals and mixtures thereof.

Fuel cells according to this invention therefore may include potassium hydroxide (KOH) electrolyte, which is usable with metal fuel cells or alkali fuel cells, and can be stored in fuel cartridges. For metal fuel cells, fuel is in the form of fluid borne zinc particles immersed in a KOH electrolytic reaction solution, and the anodes within the cell cavities are particulate anodes formed of the zinc particles. KOH fuel is disclosed in United States published patent application no. 2003/0077493, entitled "Method of Using Fuel Cell System Configured to Provide Power to One or More Loads," published on Apr. 24, 2003, which is incorporated herein by reference in its entirety.

As used herein, the term "fuel supply" includes, but is not limited to, disposable cartridges, refillable/reusable cartridges, cartridges that reside inside the electronic device, cartridges that are outside of the electronic device, fuel tanks, fuel reservoirs, fuel refilling tanks, other containers that store fuel and the tubings connected to the fuel tanks, containers, the fuel cell or the electronic device that the fuel cell powers. While a cartridge is described below in conjunction with the exemplary embodiments of the present invention, it is noted that these embodiments are also applicable to other fuel supplies and the present invention is not limited to any particular type of fuel supplies.

FIG. 1 illustrates cartridge 10 for storing fuel precursors to reformat fuels, such as those to produce sodium borohydride, methanol, ammonia borane, or hydrazine. After the precursors react to produce fuel, the fuel can be used directly in the fuel cell, or be reformatted to form hydrogen. The hydrogen is then transported to a fuel cell, e.g., a PEM, to be converted into electricity and byproducts. It is understood that any fuel that can be reformed to produce hydrogen is usable with this cartridge and is therefore within the scope of this invention.

The embodiment described herein, described below are similar to those fully discussed in co-pending patent application Ser. No. 10/679,756, entitled "Fuel Cartridges and Methods for Making Same" filed on Oct. 6, 2003, and co-pending patent application Ser. No. 10/629,004, entitled "Fuel Cartridge with Flexible Liner" filed on Jul. 29, 2003, respectively. These commonly owned applications are incorporated herein by reference in their entireties.

Cartridge 10 contains chamber 12, which is divided into first compartment 14 and reactant compartment 16. The compartments are separated by movable wall 18, which has wiper 20. Wiper 20 or an elastomeric O-ring forms a seal with the inside surface of chamber 12, so that first compartment 14 is not in fluid communication with compartment 16. A movable membrane, an extensible membrane or the like can replace movable wall 18, so long as the volume of reactant compartment 16 increases while the volume of first compartment 14 decreases. Alternatively, the seal formed by wiper 20 or the O-ring can be omitted if first compartment 14 and reactant compartment 16 contain inner liners to store fuel precursors and reactant, separately. Such liners are fully disclosed in the commonly owned, co-pending '004 patent application.

First compartment 14 encases a third compartment 15. Fuel precursor reagents stored in compartments 14 and 15 are mixed to produce fuel. Storing fuel in the form of precursor reagents can increase storage or shelf life of the fuel cartridge, when the reagents are less corrosive than the fuel. Third compartment 15 is breakable and contains a first fuel precursor reagent. A second precursor reagent inside of compartment 14 surrounds third compartment 15. When fuel is needed, e.g., before the cartridge is attached to a fuel cell, the walls of chamber 12 can be depressed thereby breaking compartment 15 releasing the first precursor reagent into the second precursor reagent. These precursor reagents mix inside the fuel cartridge to form a reformat fuel. An optional catalyst can be provided to facilitate the reaction. The reformat fuel is then transported to reaction chamber 22 to react in the presence of another catalyst or to be heated. Suitable catalysts for the production of hydrogen include platinum or ruthenium or other metals.

Alternatively, compartment 14 provides a mixture of fuel precursor reagents that are un-reacted or only partially-reacted. In alternate embodiments, the precursor reagents do not form a fuel until heated or otherwise acted upon outside of compartments 14 and 15. Thus, as a simple precursor mixture, the precursors can be heated and/or exposed to a catalyst in reaction chamber 22 to form the reformatted fuel. Precursor reagents in such alternate embodiments may also contain or be exposed to heat or catalysts at any stage outside of compartments 14 and 15 to promote the production of fuel.

Fuel and un-reacted precursor(s) can be transported by pump 24. Alternatively, the fuel and un-reacted precursor(s) can be transported through a wicking or capillary medium. Alternatively, fuel and un-reacted precursor(s) can be transported by pressure resulting from the build-up of gaseous byproduct from the precursor reagent reaction, the creation of hydrogen, or any other reaction. Transportation of fuel cell fuels by wicking or capillary action is fully disclosed in co-pending patent application Ser. No. 10/356,793, entitled "Fuel Cartridge for Fuel Cells," filed on Jan. 31, 2003. This application is incorporated herein by reference in its entirety. An optional check valve 26, i.e., one-direction flow valve, can be positioned between reaction chamber 22 and fuel precursor compartment 14.

In an alternate embodiment, the production of reformat fuel requires additional materials not stored in compartments 14 and 15. Thus a separate compartment (not shown) may store a third precursor reagent, a catalyst, a heat mixture, or surplus amounts of one of the precursor reagents or solvents found in compartments 14 and 15. These added reagents are separately transported to reaction chamber 22 by any of the above-described methods for transporting fuel and un-reacted precursors.

Reactant hydrogen gas ($H_2$) and liquid byproducts produced in reaction chamber 22 are then transported in channel 30 to reactant compartment 16 of chamber 12. Reactant compartment 16 has membrane 32, which allows hydrogen gas to pass through to internal spacing 34 inside cartridge 10. Consequently, aqueous byproducts are retained inside reactant compartment 16. As shown by the dash lines, hydrogen gas can be selectively transported out of cartridge 10 through control valve 36 to the fuel cell to produce electricity. Control valve 36 is fully disclosed in commonly owned, co-pending patent application Ser. No. 10/629,006, entitled "Fuel Cartridge with Connecting Valve," filed on Jul. 29, 2003. The disclosure of this application is incorporated herein by reference in its entirety. Membrane 32 is selected so that a certain pressure differential across the membrane is necessary for hydrogen gas to migrate across the membrane. Due to the presence of hydrogen gas, the pressure in reactant compartment 16 is higher than the pressure in fuel compartment 14 and movable wall 18 is pushed by this differential pressure to force fuel out of fuel compartment 14 to reaction chamber 22. To ensure that pressure inside reactant compartment 16 remains higher than fuel compartment 14, a poppet valve as described in the '004 application can be used in conjunction with membrane 32. Alternatively, in place of a poppet valve, a porous member, such as a filler, a foam or the like, can be used. Such porous member requires a pressure drop across it for hydrogen to move from reactant compartment 16 to internal spacing 34 and valve 36.

In this embodiment, when hydrogen fuel is no longer needed, valve 36 is shut off. Hydrogen in internal spacing 34 stops flowing out and this creates a back pressure. This back pressure stops the flow into reactant chamber 16, which also stops the flow in the fluid circuit. This stops the reaction and fuel production. When fuel is needed again, valve 36 is opened and pressurized hydrogen gas flows out of the cartridge, and this drops the pressure in internal spacing 34, which allows hydrogen gas to flow from reactant chamber 16 to internal spacing 34. This flow again pulls fuel from fuel compartment 14 to reaction chamber 22 to re-start the reaction. Pump 24 can be used to meter the flow of fuel from compartment 14 by knowing the flow rate(s) through the pump and the time that the pump is on. Cartridge 10 may also have relief valve 33, such as a poppet valve, which is configured to open when the pressure in internal spacing reaches a predetermined level.

Referring again to FIG. 1, cartridge 10 may further contain at least one breakable fourth compartment 17, containing a precursor that can be the same or different from the precursor in third compartment 15. In one embodiment, where compartments 15 and 17 contain the same precursor, fuel is first produced (as more generally described above) by reacting the precursor reagent from compartment 15 with an excess amount of the precursor that surrounds compartment 15. Fourth compartment 17, which is breakably secured to the inside wall of compartment 14, releases additional precursor reagent when it is subsequently broken off. This is accomplished as byproduct gas contents in compartment 16 increase and push movable wall 18 further into compartment 14. As a result, breaking member 41 disposed on wall 18 moves toward and breaks compartment 17 to release or create additional precursor reagent therefrom. Mixing with the remaining precursor within compartment 14, the released precursor reagent from compartment 17 creates a fresh supply of fuel. Used in this fashion, a series or an array of breakable or pierceable compartments such as compartment(s) 17 may be employed to provide a continual and extended supply of fuel. Compartments 17 can also be used in place of compartment 15. Alternatively, compartment(s) 17 are detachable and are connected to the walls of compartment 14 by a tearable or weakened section, so that when movable wall 18 contacts a detachable compartment 17, detachable compartment 17 is detached preferably along the weakened section to release the precursor reagent contained herein. The weakened section can be a section with less thickness, which can be a tear strip.

Suitable materials for compartments 15 and 17 include glass (for breakable compartments), and natural rubber (for breakaway compartments), polyethylene (including low density to high density PE), ethylene propylene (EP), EPDM and other thin polymeric films (for pierceable compartments). In one embodiment, the polyethylene in such pierced chambers is fluorinated and is substantially free of metal ions to ensure low permeation. The polyethylene can be laminated with a vapor barrier layer, such as aluminum foil or fluorine treated plastics, to reduce, for example, methanol permeation.

In the embodiment shown in FIG. 1, when the produced fuel can be used directly by the fuel cell, e.g., methanol fuel and DMFC, reaction chamber 22 and reactant compartment 16 and related components can be omitted. In other words, fuel cartridge may simply comprise first component 14, containing a first precursor reagent and third compartment 15 containing a second precursor reagent. Third component 15 is breakable so that the reagents are mixed before the cartridge is connected to a fuel cell.

Figure 2:
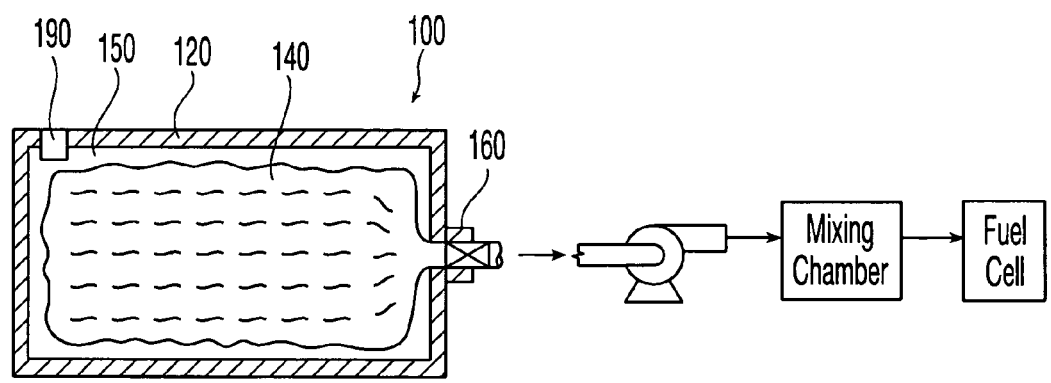
FIG. 2 is a cross-sectional view of another fuel cartridge in accordance with another embodiment of the present invention having a single precursor reagent compartment.

Another embodiment of a fuel supply in accordance with the present invention, which has a single precursor reagent compartment, is shown in FIG. 2. Cartridge 100 has a chamber 120, which holds liner 140. Liner 140 holds a first fuel precursor reagent that can be delivered to an external reaction chamber to mix with other precursor reagent(s) through valve 160. Valve 160 can be provided to control the transport of precursor reagent out of liner 140. Valve 160 can have any construction. Preferably, valve 160 is substantially similar to valve 36, discussed above. Alternatively, a second precursor reagent can be introduced into liner 140 through valve 160 to create fuel within the cartridge before the cartridge is connected to a fuel cell.

In accordance with another aspect of the invention, the cartridge may comprise two or more compartments. As shown in FIG. 3, fuel cartridge 210 may have compartments 246 and 248, where one compartment is located on top of the other compartment. Preferably, one contains a first precursor and the other contains a second precursor. A filler insert is included in each compartment to transport the precursors out of the cartridge by capillary action. In the embodiment shown in FIG. 3, the connecting column 250 of compartment 248 is disposed concentrically inside connecting column 252 of compartment 246. Preferably, column 250 is isolated from column 252 by a liquidproof film. As shown, each column is connected to capillary disks to ensure that the liquid contained therein is wicked out of the compartments. Alternatively, the compartments can be positioned side-by-side, such as compartments 254 and 256 illustrated in FIG. 4 and the compartments can have liners to store fuel, as illustrated in FIG. 4A. Each compartment 254, 256 contains a filler insert comprising a connecting column 258, 260, respectively, and capillary disks to wick the liquids out of the compartments. The cartridges in FIGS. 3 and 4 are disclosed in the co-pending '793 patent application previously incorporated herein by reference. In these embodiments, the two precursor streams are pumped into external mixing chamber 262. These embodiments are suitable for non-reformat fuel or fuels that can be pumped directly into the fuel cell, e.g., methanol. When pumps are used, the filler or wicking materials may be omitted.

Pumps useful for this invention are described in the commonly owned, co-pending '756 application previously incorporated herein by reference. A suitable pump is a micro-electro-mechanical-system (MEMS) piezoelectric pump. The precursor reagents combine either at the fuel cell or at any location upstream from it. Thus, in a preferred embodiment, two reagents combine prior to flow into the fuel cell as discussed in FIGS. 3 and 4.

It is noted that the present invention may use any number of compartments to contain any type of precursor reagent or precursor reagent mixture. For example, the fuel cartridge may have multiple inner liners. In another example, the fuel cartridge may have a first inner liner or other internal compartment for a solid precursor reagent and a second inner liner or other internal compartment for an appropriate complimentary liquid precursor reagent.

Illustrative examples of several fuel cell fuel precursor reagents suitable for use in accordance with the present invention include the following examples:

EXAMPLE 1

In Situ Production of Borohydrides

One aspect of the present invention allows for in situ formation of borohydrides (including various salts such as, but not limited to, ammonium borohydride, calcium diborohydride, and sodium borohydride) according to several known processes for producing various borohydrides.

As mentioned above, sodium borohydride is a reformat fuel cell fuel that reacts to produce hydrogen according to the following chemical formula:

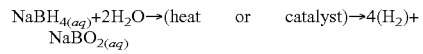

The present invention accordingly provides for in situ production of sodium borohydride (and other borohydrides) so that it can be used in such a reaction to produce hydrogen. Several processes describing the production of borohydrides are generally set forth in U.S. Pat. Nos. 6,433,129 and 6,586,563, which are incorporated herein by reference in their entireties. For example, according to the '563 patent sodium carbonate can be reacted with diborane to produce sodium borohydride:

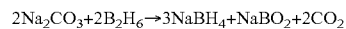

Hence, diborane and aqueous solutions of sodium carbonate can be the first and second precursor reagents to produce a borohydride.

More generally, the '563 patent also teaches, among other things, a process for producing borohydride compounds that includes the reaction of a carbonate of the formula $Y_2CO_3$ in aqueous solution at a temperature of about $-5°$ to about $20°$ C. with diborane to produce the borohydride $YBH_4$, where Y is a monovalent cationic moiety. Thus, several potential precursor reagent combinations for ambient and cold formation of borohydride salts are known.

Diborane can be stored and used as a precursor reagent for the present invention in polymer form. U.S. Pat. No. 3,928,293, which is incorporated herein by reference in its entirety, discloses solid crosslinked thiohydrocarbon borane hydride polymers and their use as reducing agents for aldehydes, ketones, lactones, oxides, esters, carboxylic acids, nitrites and olefins. These borane polymers, although stable at room temperature, can release borane ($BH_3$) under conditions of reduced pressure or heat and are disclosed as being useful as a convenient means of storing borane. Other polymers useful as precursor reagents for the production of borane are taught in U.S. Pat. Nos. 3,609,191 and 4,410,665, which are both incorporated herein by reference in their entireties.

These borane polymer complexes are less reactive as diborane, but will, with increased temperature or reaction time, enter into essentially the same reactions as diborane. Because they are water soluble, when mixed with aqueous sodium carbonate they will produce sodium borohydride according to the following chemical equation:

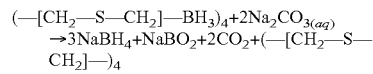

As seen, a thiohydrocarbon polymer associated with borane reacts with aqueous sodium carbonate to produce sodium borohydride. Thus, polymers such as the ones described in the '293 patent, when stored in tandem with sodium carbonate as two fuel precursor reagents, are suitable for storage and use in the fuel supplies of the present invention.

Alternatively, other precursors amenable to reduction by borane may be used with these polymers. In an alternative embodiment, for example, any other borohydride such as ammonium borohydride, calcium borohydride, or others may be produced instead of sodium borohydride by using various respective carbonate salts as a complimentary precursor reagent.

Other combinations of precursors known in the art to form borohydrides can also be used with this invention.

EXAMPLE 2

In Situ Production of Methanol Fuel Mixtures

Another aspect of the present invention allows for in situ formation of methanol. Methanol is usable in many types of fuel cells, e.g., DMFC, enzyme fuel cell, reformat fuel cell, among others. As mentioned above, direct methanol fuel cells react according to the following chemical formula:

$$CH_3OH + 1.5O_2 \rightarrow CO_2 + 2H_2O$$

To produce methanol, dimethyl dicarbonate and water are used as precursor reagents. Also known as dimethylpyrocarbonate, dimethyl dicarbonate ("DMDC") is marketed by Bayer AG under the trade name VELCORIN®. DMDC breaks down rapidly in aqueous environments. DMDC is taught as a cold sterilant in U.S. Pat. Nos. 6,563,207 and 5,866,182 and United States published patent application no. 2002/0012737, all of which are incorporated herein by reference in their entireties.

When reacted with water at ambient temperatures, DMDC breaks down into methanol and carbon dioxide. Thus, the ambient decomposition of DMDC ($(CH_3OCO)_2O$) into methanol occurs according to the following chemical equation:

$$(CH_3OCO)_2O + H_2O \rightarrow 2CH_3OH + 2CO_2$$

Because this process occurs at room temperature, the formation of methanol can be achieved for use in various fuel supplies for electronics devices that operate at room temperature. Unlike methanol, moreover, DMDC is less corrosive. For instance, because it is less corrosive than methanol it can be less harmful to containment materials, such as seals, o-rings and overall packaging materials, especially during long periods of storage prior to its use as a precursor to fuel for a fuel cell. As such, DMDC is well-suited for use as a chemical precursor reagent for fuel cells that use methanol and water as fuel. For example, when combined with a molar excess amount of water, DMDC will produce methanol and carbon dioxide (which can be vented or used to pressurize the cartridge as needed) leaving the excess water to react with methanol as part of an overall fuel cell reaction, e.g., DMFC. Alternatively, other precursors amenable to the formation of methanol may be used in this aspect of the invention.

Moreover, in situ production of methanol can be accomplished using any fuel supply, including but not limited to, the embodiments described above.

Other examples of fuel cell fuels that can be stored in the fuel supply as precursor reagents include, but are not limited to, ammonia borane and hydrazine. These fuels can be reformatted into hydrogen. Ammonia borane can be reformatted at temperatures of 100° C. and above, and hydrazine can be reformatted at room temperature, but itself requires temperatures of 100° C. and above for its creation. They can both be used in power generation and automotive applications among others.

Ammonia borane reacts as follows to form hydrogen:

$$NH_3BH_3 + H_2O + heat \rightarrow NH_2BH_{2(solid)} + H_2$$

This reaction is fully described in "Analysis of Hydrogen Production Using Ammonia and Ammonia-Borane Complex for Fuel Cell Applications," Hydrogen, Fuel Cells, and Infrastructure Technologies, FY 2002 Progress Report, Ali T-Raissi, at http://www.eere.energy.gov/hydrogenandfuelcells/pdfs/33098 sec5.pdf, and in "Portable Hydrogen Generator," The Alchemist, 30 Sep. 2003, Tina Walton, available at http://www.chemweb.com/alchem/articles/1063811899357.html. These references are incorporated herein by reference in their entireties. Ammonia borane can be produced from the following reaction:

$$2NH_{3(aq)} + B_2H_{6(aq)} \rightarrow 2NH_3BH_{3(aq)}$$

Hence, ammonia and diborane are the precursor reagents that can react in water to form ammonia borane fuel. As discussed in Example 1, several borane-containing polymers disclosed in the '293 patent can be substituted for diborane.

Hydrazine is soluble in water and decomposes to form hydrogen as follows:

$$N_2H_4H_2O + H_2O \rightarrow 2H_2 + N_2 + 2H_2O$$

Hydrazine can be produced from methylethylazine hydrolysed at high temperature, as follows:

$$(CH_3C_2H_5CN)_2 + 3H_2O + heat \rightarrow N_2H_4H_2O + 2CH_3C_2H_5CO$$

Methylethylazine is formed from hydrogen peroxide, ammonia, and methyl ethyl ketone (MEK) at room temperature, as follows:

$$H_2O_2 + 2NH_3 + 2CH_3C_2H_5CO \rightarrow (CH_3C_2H_5CN)_2 + 4H_2O$$

Hence, hydrogen peroxide, ammonia and MEK can be stored as precursor reagents to hydrazine. The reaction to produce hydrazine is described in U.S. Pat. No. 6,517,798, which is incorporated herein by reference in its entirety.

All of the above Examples have various alternative embodiments encompassed by the present invention.

While it is apparent that the illustrative embodiments of the invention disclosed herein fulfill the objectives of the present invention, it is appreciated that numerous modifications and other embodiments may be devised by those skilled in the art. Additionally, feature(s) and/or element(s) from any embodiment may be used singly or in combination with other embodiment(s). Therefore, it will be understood that the appended claims are intended to cover all such modifications and embodiments that would come within the spirit and scope of the present invention.

We claim:

1. A fuel supply for a fuel cell allowing in situ production of fuel, comprising:
    a first compartment that contains a first precursor reagent; and
    a second compartment that contains a second precursor reagent;
    wherein the contents of the first compartment and the second compartment are mixable to create a fuel for a fuel cell; and
    wherein the fuel created contains substantially no free hydrogen.

2. The fuel supply of claim 1 wherein the first compartment encases the second compartment.

3. The fuel supply of claim 1 wherein the first and second compartments are side-by-side.

4. The fuel supply of claim 1 wherein the first and second compartments are top and bottom compartments.

5. The fuel supply of claim 1 wherein the second compartment comprises a breakable or a pierceable component.

6. The fuel supply of claim 1 further comprising a third compartment that contains an additional amount of the second precursor reagent, an additional amount of the first precursor reagent, a third precursor reagent, or a catalyst.

7. The fuel supply of claim 1 wherein the fuel comprises methanol.

8. The fuel supply of claim 7 wherein the first precursor reagent comprises dimethyl dicarbonate.

9. The fuel supply of claim 7 wherein the second precursor reagent comprises water.

10. The fuel supply of claim 1 wherein the fuel comprises borohydride.

11. The fuel supply of claim 10 wherein the first precursor reagent comprises a borane-containing polymer.

12. The fuel supply of claim 10 wherein the second reagent comprises carbonate.

13. The fuel supply of claim 1 wherein the fuel comprises ammonia borane.

14. The fuel supply of claim 13 wherein the first precursor reagent comprises a borane-containing polymer.

15. The fuel supply of claim 13 wherein the second reagent comprises ammonia.

16. The fuel supply of claim 1 wherein the fuel comprises hydrazine.

17. The fuel supply of claim 16 wherein the first precursor reagent comprises an azine, hydrogen peroxide, or ammonia.

18. The fuel supply of claim 1 wherein the fuel supply is connectable to a fuel cell system.

19. The fuel supply of claim 1 wherein the second compartment is detachable.

20. The fuel supply of claim 19, wherein the second compartment comprises a weakened section.

21. The fuel supply of claim 20, wherein the weakened section has a thickness less than a thickness of the second compartment.

22. The fuel supply of claim 1, wherein the fuel created is convertible to hydrogen.

23. The fuel supply of claim 1 wherein the fuel supply is substantially free of fuel prior to the in situ mixing of the first precursor reagent and the second precursor reagent.

24. A fuel cell fuel system, comprising:
a fuel supply having a first compartment that contains a first precursor reagent; and
a second compartment that contains a second precursor reagent;
wherein the contents of the first compartment and the second compartment are mixable to create a fuel for a fuel cell; and
wherein the fuel created contains substantially no free hydrogen.

25. The fuel cell fuel system of claim 24 wherein the second compartment is part of the fuel supply.

26. A fuel supply for a fuel cell allowing in situ production of fuel, comprising:
a first compartment that contains a first precursor reagent; and
a second compartment that contains a second precursor reagent;
wherein the contents of the first compartment and the second compartment are mixable to create a fuel for a fuel cell; and
wherein the fuel created is selected from the group consisting of borohydride, ammonia borane, and hydrazine.

27. The fuel supply of claim 26 wherein the fuel is borohydride, and wherein the first precursor reagent comprises a borane-containing polymer and the second precursor reagent comprises carbonate.

28. The fuel supply of claim 26 wherein the fuel is ammonia borane, and wherein the first precursor reagent comprises a borane-containing polymer and the second precursor reagent comprises ammonia.

29. The fuel supply of claim 26 wherein the fuel is hydrazine, and wherein the first precursor reagent comprises an azine, hydrogen peroxide, or ammonia.

30. A fuel supply for a fuel cell allowing in situ production of fuel, comprising:
a first compartment that contains dimethyl dicarbonate; and
a second compartment that contains water;
wherein the contents of the first compartment and the second compartment are mixable to create methanol.

* * * * *